US00PP34023P3

(12) United States Plant Patent
Schoone

(10) Patent No.: US PP34,023 P3
(45) Date of Patent: Mar. 15, 2022

(54) ***PHALAENOPSIS* PLANT NAMED 'TRUE HERO'**

(50) Latin Name: *Phalaenopsis hybrida*
Varietal Denomination: True Hero

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 17/339,968

(22) Filed: Jun. 5, 2021

(65) Prior Publication Data

US 2021/0385994 P1 Dec. 9, 2021

Related U.S. Application Data

(60) Provisional application No. 62/705,003, filed on Jun. 6, 2020.

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
CPC ... A01H 5/02; A01H 5/00; A01H 5/08; A01H 6/62
See application file for complete search history.

(56) References Cited

U.S. PATENT DOCUMENTS

PP25,159 P3 * 12/2014 Schoone ..... A01H 5/02 Plt./311

* cited by examiner

*Primary Examiner* — June Hwu
(74) *Attorney, Agent, or Firm* — C. Anne Whealy

(57) ABSTRACT

A new and distinct cultivar of *Phalaenopsis* plant named 'True Hero', characterized by its upright plant habit; moderately vigorous to vigorous growth habit; strong flowering stems; strong leaves; freely flowering habit with typically two inflorescences per plant, each inflorescence with numerous flowers; large reddish purple-colored flowers densely covered with vivid reddish purple-colored venation; and good postproduction longevity.

2 Drawing Sheets

Figure 1:
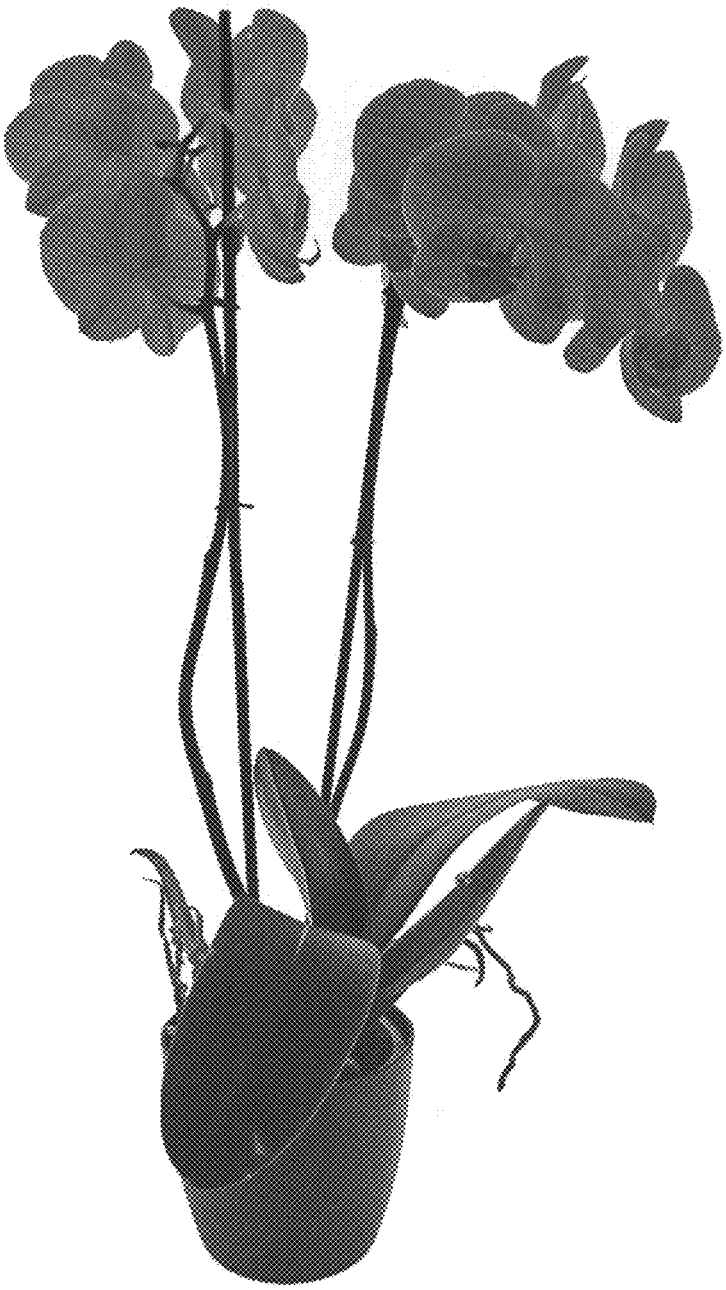

Botanical designation: *Phalaenopsis hybrida.*
Cultivar denomination: 'TRUE HERO'.

CROSS-REFERENCED TO CLOSELY-RELATED APPLICATIONS

Title: Varieties of *Phalaenopsis* Plants
Inventor: René Schoone
Filed: Jun. 6, 2020
Ser. No.: 62/705,003
Inventor and Applicant/Assignee hereby claims the benefit of this provisional U.S. Patent Application.

STATEMENT REGARDING PRIOR DISCLOSURES BY INVENTOR and APPLICANT/ASSIGNEE

An European Community Plant Breeder's Rights application for the instant plant was filed by the Applicant/Assignee of the instant application, Floricultura B.V. of Heemskerk, The Netherlands on Sep. 17, 2020, application number 2020/2196. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'True Hero'.

The new *Phalaenopsis* plant is a product of a planned breeding program conducted by the Inventor in De Lier and Heemskerk, The Netherlands. The objective of the breeding program is to develop new fast-growing and freely flowering *Phalaenopsis* plants with good leaf shape and large flowers with unique and attractive patterns and coloration.

The new *Phalaenopsis* plant originated from a cross-pollination in April, 2014 in De Lier, The Netherlands of a proprietary selection of *Phalaenopsis hybrida* identified as code number B 3374, not patented, as the female, or seed, parent with a proprietary selection of *Phalaenopsis hybrida* identified as code number GE 123, not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in March, 2017.

Asexual reproduction of the new *Phalaenopsis* plant by in vitro meristem propagation in a controlled environment in Assendelft, The Netherlands since March, 2018 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'True Hero'. These characteristics in combination distinguish 'True Hero' as a new and distinct *Phalaenopsis* plant:

1. Upright plant habit.
2. Moderately vigorous to vigorous growth habit.
3. Strong flowering stems.
4. Strong leaves.
5. Freely flowering habit with typically two inflorescences per plant, each inflorescence with numerous flowers.
6. Large reddish purple-colored flowers densely covered with vivid reddish purple-colored venation.
7. Good postproduction longevity.

Plants of the new *Phalaenopsis* can be compared to plants of the female parent selection. Plants of the new *Phalaenopsis* differ primarily from plants of the female parent selection in flower shape as flower petals of plants of the new *Phalaenopsis* are not imbricate whereas flower petals of plants of the female parent selection are touching. In addition, the curvature of the labellum is stronger in plants of the new *Phalaenopsis* than plants of the female parent selection.

Plants of the new *Phalaenopsis* can be compared to plants of the male parent selection. Plants of the new *Phalaenopsis* differ primarily from plants of the male parent selection in flower color as flowers of plants of the new *Phalaenopsis* have more prominent and distinct venation than flowers of plants of the male parent selection.

Plants of the new *Phalaenopsis* can be compared to plants of *Phalaenopsis hybrida* 'Flashdance', (U.S. Plant Pat. No. 25,159). In side-by-side comparisons, plants of the new *Phalaenopsis* differ primarily from plants of 'Flashdance' in flower flower color as flowers of plants of the new *Phalaenopsis* have more prominent and distinct venation than flowers of plants of 'Flashdance'. In addition, leaves of plants of the new *Phalaenopsis* are longer than leaves of plants of 'Flashdance'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'True Hero' grown in a container.

Figure 2:
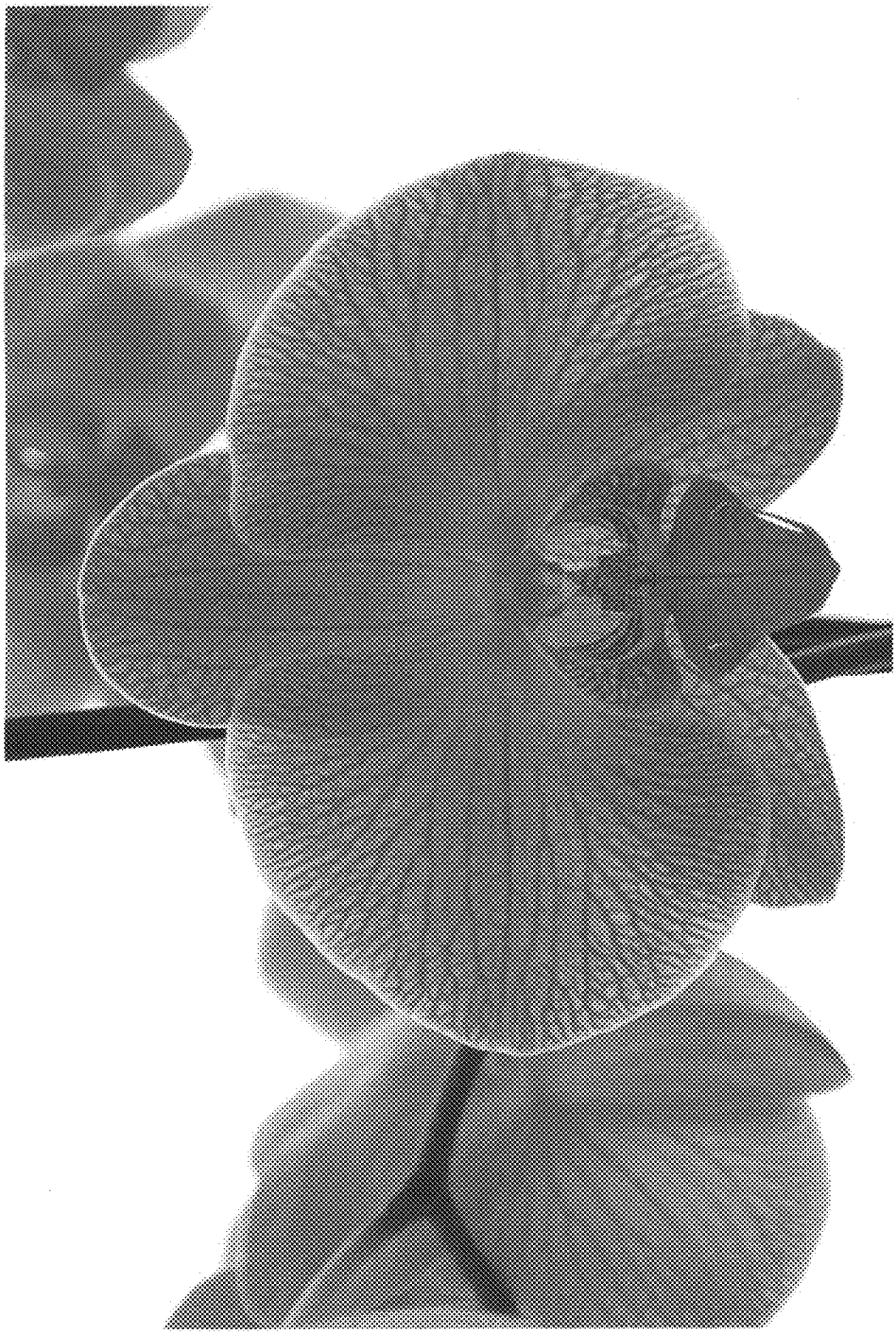

The photograph on the second sheet (FIG. 2) is a close-up view of a typical flower of 'True Hero'.

DETAILED BOTANICAL DESCRIPTION

The aforementioned photographs and following observations and measurements describe plants grown during the autumn in 10.5-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the 18 months of production, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'True Hero'.

Parentage:

*Female parent*.—Proprietary selection of *Phalaenopsis hybrida* identified as code number B 3374, not patented.

*Male parent*.—Proprietary selection of *Phalaenopsis hybrida* identified as code number GE 123, not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thick, fibrous; typically grey to green in color; actual color of the roots is dependent on substrate composition, water quality, fertilizer, substrate temperature and age of roots.

*Rooting habit*.—Low amount of branching; medium density.

Plant description:

*Plant form and growth habit*.—Herbaceous epiphyte; upright plant habit with typically two inflorescences per plant, each inflorescence with numerous flowers; monopodial; moderately vigorous to vigorous growth habit and moderate growth rate.

*Plant height, substrate level to top of foliar plane*.—About 15.6 cm.

*Plant height, substrate level to top of inflorescences*.—About 50.7 cm.

*Plant diameter or spread*.—About 32.1 cm.

Leaf description:

*Arrangement and quantity*.—Distichous, simple; sessile; about five leaves per plant.

*Length*.—About 24.2 cm.

*Width*.—About 7.8 cm.

*Aspect*.—Upright to outwardly arching.

*Shape*.—Narrowly oblong to narrowly obovate; slightly carinate.

*Apex*.—Unequal broadly acute.

*Base*.—Sheathing. Sheath length: About 2 cm. Sheath width: About 1.5 cm. Sheath color: Close to 143B tinged with close to 182B to 182C.

*Margin*.—Entire; not undulate.

*Texture and luster, upper and lower surfaces*.—Smooth, glabrous; slightly glossy.

*Venation pattern*.—Camptodromous.

*Color*.—Developing leaves, upper surface: Close to between NN137B and 146A; distally, margins tinged with close to N186C. Developing leaves, lower surface: Close to 146B; towards the margins, apex, base and main vein, strongly tinged with close to N186C. Fully expanded leaves, upper surface: Close to 137B; venation, close to 137A to 137B. Fully expanded leaves, lower surface: Close to between 143A and 146B; towards the margins, apex and main vein, slightly tinged with close to N186C; lateral venation, close to 147B slightly tinged with close to N186C.

Inflorescence description:

*Appearance and flowering habit*.—Showy zygomorphic flowers arranged on axillary branched racemes; typically two inflorescences per plant; each inflorescence with about seven flowers; flowers face outwardly on arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about eight weeks on the plant; flowers not persistent.

*Inflorescence length* (*lowermost flower to inflorescence apex*).—About 26.3 cm.

*Inflorescence width*.—About 15.2 cm.

*Flower buds*.—Height: About 2.8 cm. Diameter: About 2.1 cm by 2.7 cm. Shape: Broadly ovate. Color: Close to N77B; towards the apex, tinged with close to N79C; color becoming closer to between 181D and 197D with development.

*Flower size*.—Large, about 8.5 cm (vertical) by 10 cm (horizontal).

*Flower depth*.—About 3 cm.

*Petals, quantity and arrangement*.—Three, two lateral petals and one center petal transformed into a labellum.

*Lateral petals*.—Length: About 4.8 cm. Width: About 6.2 cm. Shape: Lunate to reniform. Apex: Shallowly retuse to obtuse. Margin: Entire. Texture and luster, upper and lower surfaces: Smooth, glabrous, velvety; matte. Color: When opening, upper surface: Close to N78B; towards the margins and apex, close to N78C; towards the base, close to N80C and at the base (at column connection), close to N78B; venation, close to NN78A. When opening, lower surface: Close to N78D; towards the margins and apex, close to N78C; towards the base, close to 76B to 76C; venation, close to N78A. Fully opened, upper surface: Close to N78B; towards the margins and apex, close to N78C; towards the base, close to N80C and at the base (at column connection), close to N78B; venation, close to N78A and NN78A. Fully opened, lower surface: Close to N80C; towards the margins and apex, close to N78C; towards the base, close to 76A to 76B; venation, close to NN78B.

*Labella*.—Appearance: Three-parted with two lateral lobes and a central lobe. Length, lateral lobes: About 2.4 cm. Width, lateral lobes: About 1.7 cm. Length, central lobe: About 3.7 cm. Width, central lobe: About 8 mm to 24 mm. Shape, lateral lobes: Obovate. Shape, central lobe: Deltoid. Apex, lateral lobes: Obtuse. Apex, central lobe: Cleft with two narrow and strongly recurved cirrose tips, about 1.5 cm in length and about 1.7 mm in width. Margins, lateral lobes: Entire; coarsely undulate. Margins, central lobe: Entire. Texture and luster, upper and lower surfaces: Smooth, glabrous, moderately velvety; matte. Callosities: Located at the base of the labellum and attachment point of the lateral petals; about 5 mm in length, about 6.5 mm in width and about 6 mm in height. Color: When opening, upper surface: Lateral lobes: Close to 77C; towards the apex, close to 77D; basal margin, tinged with close to 70B; stripes at the base, close to 71A; venation, close to N78A. Central lobe: Close to N78A; towards the margins, tinged with close to 177C; at the base (at column connection), close to N155B with radial stripes, close to 71A; main vein, close to N79B; lateral venation, close to N79C; cirrose tips, close to N78A. Callosities: Close to 11A densely covered with fine dots, close to 59A. When opening, lower surface: Lateral lobes: Close to N75B; basal margin, tinged with close to N77B; towards the base, close to between 75D and N155A; venation, close to N78B. Central lobe: Close to N78B; towards the margins, slightly tinged with close to 177C; at the base (at column connection), close to between 75D and N155A; venation, close to N78A; cirrose tips, close to N78B. Fully opened, upper surface: Lateral lobes: Close to 77C; towards the apex, close to 77D; basal margin, tinged with close to 70B; towards the base, tinged with close to 11A with stripes, close to 71A; venation, close to N78A. Central lobe: Close to N78A to slightly lighter than N78A; towards the margins, tinged with close to 177C; at the base (at column connection), close to N155B with radial stripes, close to 71A; main vein, close to N79B; lateral venation, close to N79C; cirrose tips, close to N78A. Callosities: Close to 13C densely covered with fine dots, close to 59A. Fully opened, lower surface: Lateral lobes: Close to N75B; basal margin, tinged with close to N77B; towards the base, close to between 75D and N155A; venation, close to N78B. Central lobe: Close to N78B; towards the margins, slightly tinged with close to 177C; at the base (at column connection), close to between 75D and N155A; venation, close to N78A; cirrose tips, close to N78B.

*Sepals*.—Quantity and arrangement: Three, one upper dorsal sepal and two lower lateral sepals. Length, dorsal sepal: About 5 cm. Width, dorsal sepal: About 3.5 cm. Length, lateral sepals: About 5 cm. Width, lateral sepals: About 3.1 cm. Shape, dorsal sepal: Broadly elliptic to slightly ovate. Shape, lateral sepals: Ovate. Apex, dorsal sepal: Obtuse. Apex, lateral sepals: Bluntly acute. Base, dorsal sepal: Truncate. Base, lateral sepals: Cuneate to truncate.

Margin, dorsal and lateral sepals: Entire. Texture and luster, dorsal and lateral sepals, upper and lower surfaces: Smooth, glabrous, velvety; matte. Color, dorsal sepal: When opening, upper surface: Close to N78B; towards the margins and apex, close to N78C; towards the base, close to N78D and at the base (at column connection), close to N78B; venation, close to NN78A. When opening, lower surface: Close to N78C; central blotch, tinged with close to N79C; venation, close to N78A. Fully opened, upper surface: Close to N78B; towards the base, close to N78D and at the base (at column connection), close to N78B; venation, close to N78A. Fully opened, lower surface: Close to between N78B and N78C; central blotch, tinged with close to N79B; towards the base, close to between N78C and N78D; venation, close to N78B. Color, lateral sepals: When opening, upper surface: Close to N78B; towards the margins and apex, close to N78C; towards the base, close to N78D and at the base (at column connection), close to N78B; venation, close to NN78A. When opening, lower surface: Close to N78C; towards the base, tinged with close to 75A; main vein, close to N79C; lateral venation, close to N78B. Fully opened, upper surface: Close to N78C; towards the base, close to N75B and at the base (at column connection), close to N78C; venation, close to N78A. Fully opened, lower surface: Close to between N78B and N78C; towards the base, close to N78D; main vein, close to N78A; lateral venation, close to N78B.

*Peduncles*.—Length: About 55.5 cm. Diameter: About 6 mm. Strength: Strong. Aspect: Upright to outwardly arching. Texture and luster: Smooth, glabrous; matte. Color: Close to N199B with fine dots, close to 147B.

*Pedicels*.—Length: About 3.8 cm. Diameter: About 3 mm. Strength: Moderately strong. Aspect: About 55° from peduncle axis. Texture and luster: Smooth, glabrous; matte. Color: Close to N75B to N75C; proximally, close to between N186C and 200B.

*Reproductive organs*.—Androecium: Column length: About 9 mm. Column width: About 6 mm. Column color: Close to N78A; proximally, close to N78C; distal blotch, close to 76B. Pollinia quantity: Two. Pollinia diameter (per two pollinia): About 2.5 mm. Pollinia color: Close to 24A. Gynoecium: Stigma length: About 3.5 mm. Stigma width: About 4.5 mm. Stigma shape: Reniform. Stigma color: Close to N155A. Ovary length: About 8 mm. Ovary diameter: About 1 mm. Ovary color: Close to 157A. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate temperatures ranging from about 15° to about 40° C. and are suitable for USDA Hardiness Zones 10 to 12.

It is claimed:

1. A new and distinct *Phalaenopsis* plant named 'True Hero' as illustrated and described.

* * * * *